(12) United States Patent
Holmes et al.

(10) Patent No.: US 6,458,985 B1
(45) Date of Patent: Oct. 1, 2002

(54) USE OF COMPRESSED $CO_2$ IN CHEMICAL REACTIONS

(75) Inventors: Andrew Bruce Holmes, Cambridge; Andrew Ian Cooper, Liverpool; Michael Andrew Carroll, London, all of (GB)

(73) Assignee: Cambridge University Technical Services, Ltd. (GB)

(*) Notice: Subject to any disclaimer, the term of this patent is extended or adjusted under 35 U.S.C. 154(b) by 0 days.

(21) Appl. No.: 09/627,759

(22) Filed: Jul. 28, 2000

Related U.S. Application Data

(63) Continuation of application No. PCT/GB99/00294, filed on Jan. 28, 1999.

(30) Foreign Application Priority Data

Jan. 28, 1998 (GB) ............................................. 9801665
Jan. 30, 1998 (GB) ............................................. 9801915

(51) Int. Cl.[7] ...................... C07C 315/00; C07C 319/00

(52) U.S. Cl. ........................................... 560/19; 560/51

(58) Field of Search .......................... 556/136, 13, 14, 556/64; 560/20, 19, 51, 61; 549/86, 83; 548/469, 490; 585/19, 24, 25; 526/89, 108

(56) References Cited

U.S. PATENT DOCUMENTS

| | | | |
|---|---|---|---|
| 4,748,220 A | 5/1988 | Hartmann et al. | |
| 5,066,684 A | 11/1991 | LeMay | |
| 5,128,382 A | 7/1992 | Elliott, Jr. et al. | |
| 5,629,353 A | 5/1997 | Steckle, Jr. et al. | |
| 5,679,737 A | 10/1997 | DeSimone et al. | |

FOREIGN PATENT DOCUMENTS

| | | |
|---|---|---|
| WO | 9601851 | 7/1995 |
| WO | 9832533 | 1/1997 |

OTHER PUBLICATIONS

Carroll et al., Chem. Commun., 1998, p. 1395–1396.*
Morita et al., Chem. Commun., 1998, p. 1397–1398.*
Kainz, Sabine, Daniel Koch, Wolfgang Baumann, and Walter Leitner (1997) "Perfluoroalkyl–Substituted Arylphosphanes as Ligands for Homogeneous Catalysis in Supercritical Carbon Dioxide" *Angew. Chem. Int. Ed. Engl.* 36(15):1628–1630.

Fürstner, Alois, Daniel Koch, Klaus Langemann, Walter Leitner, Christian Six (1997) "Olefin Metathesis in Compressed Carbon Dioxide" *Angew. Chem. Int. Ed. Engl.* 36(22):2466–2469.

Burk, Mark J., Shaoguang Feng, Michael F. Gross, and William Tumas (1995) "Asymmetric Catalytic Hydrogenation Reactions in Supercritical Carbon Dioxide" *J. Am. Chem. Soc.* 117:8277–8278.

Cooper, Andrew I., Williams P. Hems, Andrew B. Holmes (1998) "Synthesis of cross–linked polymer microspheres in supercritical carbon dioxide" *Macromol. Rapid. Commun.* 19:353–357.

Carroll, Michael A. and Andrew B. Holmes (1998) "Palladium–catalysed carbon–carbon bond formation in supercritical carbon dioxide" *Chem. Commun.*, p. 1395–1396.

Morita, David K., David R. Pesiri, Scott A. David, William H. Glaze and William Tumass (1998) "Palladium–catalyzed cross–coupling reactions in supercritical carbon dioxide" *Chem. Commun.*, p. 1397–1398.

\* cited by examiner

*Primary Examiner*—Samuel Barts
*Assistant Examiner*—Elvis O. Price
(74) *Attorney, Agent, or Firm*—Saliwanchik, Lloyd & Saliwanchik

(57) ABSTRACT

A process for the transformation of an organic molecule catalyzed by a ligand-metal complex, is conducted in compressed CO2 as a solvent, wherein the complex comprises a perfluorinated group. Further, a process for the polymerization of a monomer containing two or more polymerizable groups, optionally together with another copolymerizable monomer, to give a cross-linked polymer in the form of essentially spherical particles, is conducted in compressed $CO_2$ as a solvent, typically in the presence of a surfactant.

19 Claims, No Drawings

US 6,458,985 B1

USE OF COMPRESSED CO₂ IN CHEMICAL REACTIONS

CROSS-REFERENCE TO A RELATED APPLICATION

This application is a continuation of international application PCT/GB99/00294 which designated the United States, with an international filing date of Jan. 28, 1999.

FIELD OF THE INVENTION

The present invention relates to the use of compressed $CO_2$ in chemical reactions. More particularly, it relates to homogeneous catalysis in compressed $CO_2$, e.g. metal-catalysed reactions, and also to the synthesis of cross-linked polymers in $CO_2$.

BACKGROUND OF THE INVENTION

Metal-catalysed processes are extremely common in the formation of organic molecules, in particular pharmaceuticals, agrochemicals, flavours, fragrances and other consumer products. The use of a coordinating ligand, in such transformations, allows control of such variables as reaction rates, asymmetric induction, solubility, functional group specificity, product distribution and the yield of the process.

Metal-catalysed processes are typically conducted in conventional organic solvents (VOCs—volatile organic compounds). However, these materials have several drawbacks associated with their use. VOCs can be expensive, toxic (benzene, chlorofluorocarbons, acetonitrile), flammable (diethyl ether), restricted in availability (CFCs), difficult to process (solvent residues) and have associated disposavrecycling problems.

Compressed carbon dioxide is an attractive solvent for the preparation of organic molecules because it is inexpensive, non-toxic, and non-flammable. Unlike conventional liquid solvents, compressed $CO_2$ is highly compressible and the density (and therefore solvent properties) can be tuned over a wide range by varying the pressure. Moreover, compressed $CO_2$ reverts to the gaseous state upon depressurisation, greatly simplifying the separation of solvent from solute(s) and thereby reducing solvent residues in the products.

The metal-catalysed formation of organic molecules, in compressed $CO_2$, has been very limited: hydrogenation [Burk et al, J. Am. Chem. Soc. (1995) 117, 8277; Jessop et al, Nature (1994) 368, 231], hydroformylation [Kainz et al, Angew. Chem. Int. Ed. Engl. (1997) 36, 1628] and others [Furstner et al, Angew. Chem. Int. Ed. Engl. (1997) 36, 2466] have been reported.

WO-A-9601851 discloses polymerisation processes, including olefin metathesis in $CO_2$. A fluorinated dispersing agent may be used.

Cross-linked polymer resins are useful in a wide range of applications, including solid-phase synthesis, combinatorial chemistry, polymer-supported reagents, molecular imprinting, size-exclusion chomatography, ion-exchange resins, medical diagnostics, and the controlled release of drugs. In all of these various applications, it is often desirable to produce the cross-linked resins in the form of uniform microspheres. This is usually achieved by heterogeneous methods such as suspension, dispersion, or emulsion polymerisation [Arshady, Colloid Polym. Sci., (1992) 270, 717]. Typically, amphiphilic surfactants or stabilisers are used to prevent particle coalescence in these processes; however, residual surfactant on the particle surfaces may sometimes impair the performance properties of the resulting polymers. The formation of uniform cross-linked polymer microspheres has been achieved in the absence of surfactants; however, the solvents employed are often toxic (e.g., acetonitrile) [Li et al, J. Polym. Sci., Part A, Polym. Chem., 1993, 31, 3257] and/or expensive (e.g. perfluorocarbons) [Zhu, Macromolecules (1996) 29, 2813].

Supercritical carbon dioxide ($scCO_2$) is an attractive solvent for polymer chemistry because it is inexpensive, non-toxic, and non-flammable [Canelas et al, Adv. Polym. Sci. (1997) 133, 103]. Unlike conventional liquid solvents, $scCO_2$ is highly compressible and the density (and therefore solvent properties) can be tuned over a wide range by varying pressure. Moreover, $scCO_2$ reverts to the gaseous state upon depressurisation, greatly simplifying the separation of solvent from solute(s). $scCO_2$ has been used as a solvent medium for homogeneous polymerisations [DeSimone et al, Science (1992) 257, 945; and PCT/US93/01626] and heterogeneous precipitation polymerisations [Romack et al, Macromolecules (1995) 28, 912]. In many cases, the precipitation polymerisation of polymers which are insoluble in $scCO_2$ occurs, to give low polymer yields and undefined, agglomerated polymer morphologies [Canelas et al, supra].

Polymeric surfactants or stabilisers have been developed which allow the synthesis of $CO_2$-insoluble polymers in $scCO_2$ in high yields by dispersion polymerisation [DeSimone et al, Science (1994) 265, 356; Canelas et al, Macromolecules (1997) 30, 5673; U.S. Pat. No. 5,679,737]. By using the appropriate surfactants or stabilisers, it was possible to generate these polymers as uniform microspheres. All of these examples relate to the polymerisation in $scCO_2$ of monomers containing a single polymerisable functional group (e.g. styrene, methyl methacrylate, acrylic acid) and not bi- or multi-functional monomers of the type known to promote cross-linking in polymerisations (e.g. divinylbenzene (DVB), trimethylol propane trimethacrylate (TRM), ethylene glycol dimethacrylate (EGDMA)).

U.S. Pat. No. 4,748,220 discloses that cross-linked polymer particles were formed in liquid or supercritical $CO_2$. The polymers were formed as pulverulent powders with primary particles in the size range 0.5–3 µm; however, the particles were not formed as regular microspheres. The use of $scCO_2$ to form cross-linked nanoporous polymer monoliths [U.S. Pat. No. 5,629,353] and microcellular cross-linked foams [U.S. Pat. Nos. 5,128,382; 4,748,220; 5,066, 684] has also been described.

SUMMARY OF THE INVENTION

A first aspect of the present invention is based on the surprising observation that the incorporation of perfluorinated chains dramatically increases the solubility of ligand-metal complexes in compressed $CO_2$, and enables metal-catalysed reactions to take place in a non-polar medium without chemical participation of the carbon dioxide. This improved solubility allows the ligand metal complexes to act as homogeneous catalysts. In particular, fluorinated phosphines are useful in palladium-catalysed processes. An application of particular value is where a reactant is immobilised on a material that swells in the presence of $CO_2$.

A second aspect of the present invention is based on the surprising discovery that a range of cross-linked polymers can be formed using compressed $CO_2$ as the polymerisation medium, and that the polymers can be isolated in high yields directly from the reaction vessel as dry, free-flowing powders, in the form of discrete, uniform microspheres. This may be done, depending on the reactants and conditions, with or without the use of added surfactants. The invention thus provides for the synthesis of a range of cross-linked copolymers in $CO_2$ for a variety of potential applications, including molecular imprinting, solid-phase synthesis, combinatorial chemistry, polymer supported reagents, size-exclusion chomatography, and medical diagnostics.

The polymerisation route is simple, polymer yields are high, the solvent can be easily separated from the products, and the procedure allows the formation of uniform polymer microspheres with diameters in the range 1–5 μm by suspension or precipitation polymerisation, from styrenic monomers, without the use of any surfactants or stabilisers. When surfactants are used, smaller particles with controlled sizes of less than 0.5 μm diameter can be formed by emulsion polymerisation.

DESCRIPTION OF THE INVENTION

The first aspect of this invention typically uses fluorinated phosphorus-derived ligands of the formula

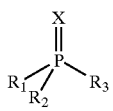

wherein X is selected from O, S and Se or may simply be an unshared pair of electrons. Preferably, X is O or S. Most preferably, is X is an unshared electron pair.

$R_1$, $R_2$ and $R_3$ may each be any non-interfering group. Examples are alkyl, aryl, heteroaryl, alkoxy, aryloxy, heteroaryloxy, thioalkyl, thioaryl, thioheteroaryl, aminoalkyl (primary, secondary, tertiary), aminoaryl, imino.

Preferably, $R_1$ or $R_2$ carries a perfluorinated carbon chain or partially fluorinated carbon, siloxy or short polyether chain. The carbon chain is a substituent in its own right or a group within the chosen substituent. It is selected from chain length C1 to C40, preferably C4 to C8 and most preferably C6. It may be branched or linear. Typically, the perfluorinated part comprises at least 1, 2, 3, 4, 5 or more C atoms.

$R_1$, $R_2$ and $R_3$ may be further modified by carrying another metal-chelating substituent such as a phosphine, nitrogen, oxygen or sulfur-based functionality or arsine.

The phosphorus in formula 1 may instead be arsenic.

For specific applications, one preference is for $R_1=R_2=CH_2CH_2C_6F_{13}$ and $R_3=Ph$. The perfluorinated group is part of the substituent.

The use of fluorinated ligands increases the solubility of ligand-metal complexes in compressed $CO_2$. It is also shown that solubility for a given complex is dependant upon the degree of fluorination. Metals that may show the effect of improved solubility with fluorinated ligands are Pd, Pt, Ni, Rh, Ru, Ir, Al, Mo, W, Re, Os, Hg, Pb, Au, Ag, Cr, Co, Mn, Mg, Zn, Fe, Zr, Ti having oxidation states in the range (0) to (8). Palladium (II), leading to a reactive palladium (0) species is preferred.

A range of catalyst concentrations may be employed in metal-catalysed processes. Typical concentrations are in the range of 0.01–50 mol % versus substrate, with preference for 1–10 mol %, specifically 1–5 mol % catalyst concentration.

The yield of product for a given process is dependant on the time of reaction, catalyst concentration, temperature and the identity of other reagents.

A range of reaction types may be conducted in compressed $CO_2$ and fluorinated ligand-metal complexes are versatile catalysts in compressed $CO_2$. Both intramolecular and intermolecular metal-catalysed processes may be conducted. Specific types of reactions that may be conducted using fluorinated ligand-metal complexes are hydrogenation, hydroboration, hydrosilylation, hydrocyanation, hydroformylation, allylic substitution, carbonylation, cross-coupling processes, cyclisation processes, conjugate addition, oxidation and epoxidation. Preferably, palladium-mediated carbon-carbon bond forming reactions take place. Most specifically, Heck [see Heck, "Palladium Reagents in Organic Synthesis", Academic Press, Orlando. 1985], Suzuki [see Migaura et al, Syn. Commun. (1981) 11, 513]; Sonogashira [see Sonogashira et al, Tetrahedron. Lett. (1975) 4467] and Stille couplings are surprisingly effective in compressed $CO_2$. This is surprising, because polar solvents are specifically preferred for the Heck reaction [see Spencer, J. Organomet. Chem. (1983) 258, 101]. Further, boronic acids of the type suitable for use in the Suzuki reaction are surprisingly soluble in $CO_2$.

For the Heck reaction, it is particularly preferred to use an aryl iodide as the substrate. As the complex, palladium acetate is preferred since it is reactive, gives good yields and can be generated in situ.

An important advantage of this invention is the surprising ease of product isolation in comparison to conventional techniques. Improvements in product separation and purification using tandem supercritical fluid extraction (SFE) and supercritical fluid chromatography (SFC) are expected. Other advantages in this area of process development may include the use of the catalysts in solid-phase synthesis.

The process of this invention is particularly suited to the use of palladium-mediated coupling reactions in compressed $CO_2$, in which there are one or more reactants supported on resins or dendrimers which undergo swelling by compressed $CO_2$. This may accelerate reaction rates and enhance mass transport within the supported reactant.

The second aspect of this invention refers to the formation of cross-linked polymers in compressed $CO_2$ (by way of example only "sc$CO_2$" may be discussed below) by the polymerisation of multi-functional monomers containing two or more polymerisable functional groups. Examples of such monomers are bi-/multi-functional styrene monomers, bi-/multi-functional methacrylate monomers, bi-/multi-functional acrylate monomers, bi-/multi-functional allyl ether monomers, bi-/multi-functional epoxide monomers, and bi-/multi-functional oxetane monomers. The most preferred monomers are divinylbenzene 1, ethylene glycol dimethacrylate 2, and trimethylol propane trimethacrylate 3

1

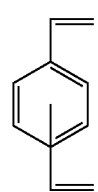

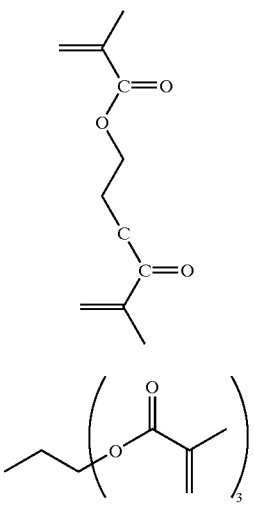

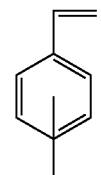

It will be evident that the polymerisation process of the invention may utilise one or more monomers. There may be one or more monomers containing two or more polymerisable groups, optionally together with one or more of other copolymerisable monomers. The weight of the cross-linker with respect to total monomer weight is typically 2–100%, preferably 40–100%. Using more than 50% of a styrenic monomer such as DVB, and a concentration of monomers in $CO_2$ of between 15 and 40 vol %, surfactant is unnecessary. If less reactive monomers, and therefore also a surfactant, are used, the monomer concentration in $CO_2$ is less critical.

The cross-linked polymers can be isolated as dry, free-flowing powders, directly from the reactor. Since the solvent, $CO_2$, reverts to a gas upon depressurisation, no solvent residues are left in the resulting cross-linked polymers, and the use of VOC solvents is avoided.

Under certain conditions, regular polymeric microspheres (1–5 μM diameter) can be formed by suspension polymerisation in the absence of any added surfactants or stabilisers. In the presence of a surfactant, highly regular cross-linked microspheres (<0.5 μm diameter) can be formed by emulsion polymerisation in $scCO_2$.

The polymerisation procedure works efficiently in $scCO_2$ when thermal-free radical initiation is used, employing 2,2'-azobisisobutyronitrile (AIBN) at 65° C. as the preferred initiator. Other free-radical initiators (either thermally or photochemically-decomposed) may be used, as may be cationic initiators, e.g. in the case of ring-opening polymerisations of oxirane/oxetane-based cross-linking monomers.

$scCO_2$ is a useful and versatile solvent for the synthesis of cross-linked resins in the form of uniform microspheres with precise control of particle size and morphology. The ease of separation of solvent from solute is an important advantage. Other advantages may include the formation of macroporous cross-linked structures by swelling with $scCO_2$, and the tuning of cross-linked particle size and morphology by the variation of $CO_2$ pressure during polymerisation. A range of cross-linked copolymers may be generated, by copolymerisation of the cross-linker with comonomers which contain surface-active or derivatisable/reactive functional groups.

Preferred comonomers of this type contain alkyl, alkyl chloride, aryl fluoride, fluoroalkyl and carboxylic acid functional groups. Specific examples are:

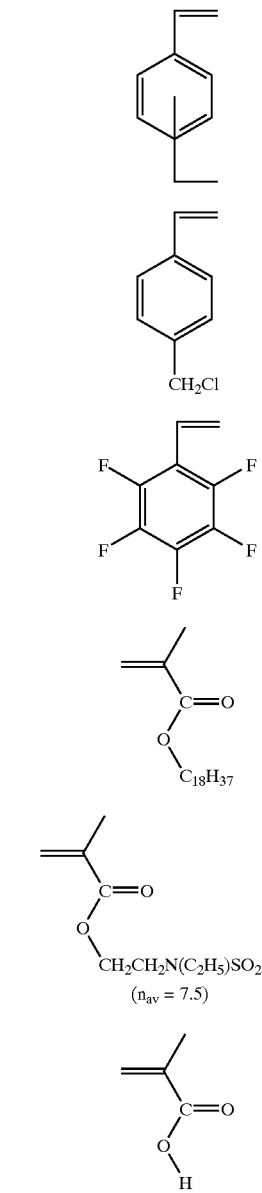

Other suitable comonomers contain poly(dimethyl siloxane) chains, low molecular weight poly(ethylene glycol) chains, perfluoropolyether chains, alkyl bromides, alkyl iodides, alcohols (alkyl and aryl), protected alcohols (alkyl and aryl), esters (alkyl and aryl), aldehydes (alkyl and aryl), amines (alkyl and aryl), amides (alkyl and aryl), crown ethers, porphyrins, fluorescent functional groups, radio-labelled functional groups, template groups for molecular imprinting, hygroscopic groups for the formation of super-absorbent polymers, functional groups for affinity chromatography, derivatisable functional groups for parallel synthesis on well-defined polymer beads, organic dyes, pharmaceutical molecules for controlled drug delivery, inorganic/organic reagents for organic synthesis, and transition metal/main group metal catalysts.

By way of example, cross-linked polymer microspheres incorporating a dispersed organic dye can be synthesised by this method. The polymer environment may contain functional groups of the type used in molecular imprinting (e.g. the carboxylic acid functionalities in a methacrylic acid comonomer). Cross-linked microspheres may incorporate other molecules, such as template molecules for molecular imprinting, pharmaceuticals for controlled release, biomolecules, fluorescent molecules, odour-releasing molecules (e.g. fragrances), rigid rod fluorophores, LED fluorescent emitters, and molecules with magnetic properties.

Any surfactant used in the invention should be soluble in $CO_2$. The amount of surfactant that is used may be, for example, 0.25 to 5% w/w, preferably about 3% w/w, with respect to monomer.

A $CO_2$-soluble, diblock copolymer surfactant has been synthesised by a modified screened anionic polymerisation (SAP) route [see Yong et al. Chem. Commun. (1997) 1811]. It has the formula

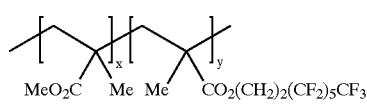

The copolymer, which contains a $CO_2$-soluble fluorinated segment and a methacrylate-based anchoring segment, was found to be highly soluble in $scCO_2$. The use of this surfactant has been shown to lead to the formation of uniform cross-linked microspheres (diameter <0.5 μm) by emulsion polymerisation in $scCO_2$. The most preferred surfactants are diblock copolymers prepared by screened anionic polymerisation consisting of a $CO_2$-soluble poly (fluoro methacrylate) block and a $CO_2$-insoluble poly (methyl methacrylate) anchoring block. Other surfactants that may be suitable use in the invention are fluorinated graft copolymers, siloxane-based graft copolymers, diblock copolymer surfactants consisting of a $CO_2$-soluble poly (fluoro methacrylate) block and a $CO_2$-insoluble poly (styrene) anchoring block, diblock copolymer surfactants consisting of a $CO_2$-soluble poly(siloxane) block and a $CO_2$-insoluble poly(methyl methacrylate) anchoring block, and diblock copolymer surfactants consisting of a $CO_2$-soluble poly(siloxane) block and a $CO_2$-insoluble poly (styrene) anchoring block.

Accordingly, cross-linked copolymers are synthesised in $scCO_2$ and can be isolated directly from the reactor in the form of uniform microspherical particles both with and, unexpectedly, without the use of added surfactants.

The following Examples illustrate the invention.

EXAMPLE (1H, 1H, 2H, 2H-perfluorooctyl)diphenylphosphine oxide

A solution of 1H, 1H, 2H, 2H-perfluorooctyl iodide (9.48 g, 20 mmol) in ether (40 ml) was added to a suspension of magnesium turnings (960 mg, 40 mmol), with a trace of iodine, also in ether (40 ml). The mixture was stirred at room temperature overnight, the stirring was stopped and the remaining solids allowed to settle. The resulting Grignard reagent, as a solution in ether, was added via cannula to a solution of chlorodiphenylphosphine (2.20 g, 10 mmol) also in ether (40 ml). This addition was accompanied by the rapid formation of a white precipitate. The mixture was stirred at room temperature for a further 3 hrs when aqueous hydrochloric acid (100 ml of a 1M solution) was added. The mixture was extracted with ether (4×250 ml) and the organic fractions combined, dried ($MgSO_4$) and concentrated in vacuo to give the crude product (7.29 g) which was used in the next step without purification.

Sodium periodate (3.0 g, 15 mmol) was added to a solution of the crude phosphine (7.29 g) in acetone (100 ml) and the mixture stirred at room temperature overnight. The solvent was removed in vacuo and water (200 ml) added, the resulting mixture was extracted with ether (4×250 ml) and the organic fractions combined, dried ($MgSO_4$) and concentrated in vacuo to give the crude product. The product was purified by flash column chromatography on silica gel, eluting with methanol-dichloromethane (5:95) to give a white crystalline solid (4.64 g, 8.47 mmol, 85%), mp ($CH_2Cl_2$) 103–105 C. (Found: M$^+$, 549.0610. $C_{20}H_{14}F_{13}PO$ requires M$^+$, 549.0653).

EXAMPLE 2

Di(1H, 1H, 2H, 2H-perfluorooctyl)phenylphosphine oxide

A solution of 1H, 1H, 2H, 2H-perfluorooctyl iodide (18.96 g, 40 mmol) in ether (80 ml) was added to a suspension of magnesium turnings (1.920 g, 80 mmol), with a trace of iodine, also in ether (40 ml). The mixture was stirred at room temperature overnight, the stirring was stopped and the remaining solids allowed to settle. The resulting Grignard reagent, as a solution in ether, was added via cannula to a solution of dichlorophenylphosphine (1.79 g, 10 mmol) also in ether (80 ml). This addition was accompanied by the rapid formation of a white precipitate. The mixture was stirred at room temperature for a further 3 hrs when aqueous hydrochloric acid (100 ml of a 1M solution) was added. The mixture was extracted with ether (4×250 ml) and the organic fractions combined, dried ($MgSO_4$) and concentrated in vacuo to give the crude product (10.18 g) which was used in the next step without purification.

Sodium periodate (3.0 g, 15 mmol) was added to a solution of the crude phosphine (10.18 g) in acetone (100 ml) and the mixture stirred at room temperature overnight. The solvent was removed in vacua and water (200 ml) added, the resulting mixture was extracted with ether (4×250 ml) and the organic fractions combined, dried ($MgSO_4$) and concentrated in vacuo to give the crude product. The product was purified by flash column chromatography on silica gel, eluting with dichloromethane to give a white crystalline solid (5.94 g, 7.26 mmol, 73%), mp ($CH_2Cl_2$) 91–93 C. (Found: M$^+$, 819.0313. $C_{22}H_{13}F_{26}PO$ requires M+, 819.0367).

EXAMPLE 3

(1H, 1H, 2H, 2H-perfluorooctyl)diphenylphosphine

Trichlorosilane (0.1 ml, 1 mmol) was added, at room temperature, to a suspension of (1H, 1H, 2H, 2H-perfluorooctyl)diphenylphosphine oxide (55 mg, 0.1 mmol) and triethylamine (0.1 ml, 0.7 mmol) in toluene (5 ml). The mixture was then heated at 100 C. overnight and then allowed to cool. Aqueous sodium hydroxide (40 ml of a 1M solution) was added and the resulting mixture extracted with ether (4×25 ml). The organic fractions were combined, dried ($MgSO_4$) and concentrated in vacuo to give the crude product. The product was purified by flash column chromatography on silica gel, eluting with hexane to give a white crystalline solid (42 mg, 0.079 mmol, 79%), mp ($CH_2Cl_2$) 44–45° C. (Found: M+,532.0600. $C_{20}H_{14}F_{13}P$ requires M+, 532.0625).

EXAMPLE 4

Di(1H, 1H, 2H, 2H-perfluorooctyl)phenylphosphine

Trichlorosilane (1 ml, 10 mmol) was added, at room temperature, to a solution of di(1H, 1H, 2H, 2H-perfluorooctyl)phenylphosphine oxide (818 mg, 1 mmol) and triethylamine (1 ml, 7.2 mmol) in toluene (40 ml). The mixture was then heated at 100 C. overnight and then allowed to cool. Aqueous sodium hydroxide (100 ml of a 1M solution) was added and the resulting mixture extracted with ether (3×250 ml). The organic fractions were combined, dried ($MgSO_4$) and concentrated in vacuo to give the crude product. The product was purified by flash column chromatography on silica gel, eluting with hexane to give a white crystalline solid (710 mg, 0.88 mmol, 88%), mp ($CHCl_3$) 37–39° C. (Found: M+, 802.0319. $C_{22}H_{13}F_{26}P$ requires M+, 802.0339).

EXAMPLE 5

Bis{(1H H,2H,2H-perfluorooctyl) diphenyliphosphino}-palladium dichloride

A solution of (1H, 1H, 2H, 2H-perfluorooctyl) diphenylphosphine (53 mg, 0.1 mmol) in chloroform (1 ml) was added to bis(acetonitrile)palladium dichloride (13 mg, 0.05 mmol). After 1 hr the solution was concentrated in vacuo to give the product as a orange crystalline solid (53 mg, 0.043 mmol, 86%), mp ($CH_2Cl_2$) 149–151 C. (Found: M+—Cl, 1205.0061. $C_{40}H_{28}C_{l2}F_{26}P_2Pd$ requires M+—Cl, 1204.9974).

EXAMPLE 6

Bis{di(1H,1H,2H,2H-perfluorooctyl) phenylphosphino-palladium dichloride

A solution of di(1H,1H,2H,2H-perfluorooctyl) phenylphosphine (401 mg, 0.5 mmol) in dichloromethane (5 ml) was added to bis(acetonitrile)palladium dichloride (65 mg, 0.25 mmol). After 1 hr the solution was concentrated in vacuo to give the product as a orange crystalline solid (435 mg, 0.244 mmol, 97%), mp ($CH_2Cl_2$) 91–93 C. (Found: M+—Cl, 1744.9402. $C_{44}H_{26}Cl_2F_{52}P_2Pd$ requires M+—Cl, 1744.9403).

EXAMPLE 7

Diphenylacetylene

Bis{di(1H,1H,2H,2H-perfluorooctyl) phenylphosphino}palladium dichloride (89 mg, 0.05 mmol), copper (I) iodide (9 mg, 0.05 mmol), iodobenzene (0.11 ml, 1 mmol), phenylacetylene (0.11 ml, 1 mmol) and triethylamine (0.15 ml, 1.1 mmol) were placed in a 10 ml stainless steel cell. The cell was sealed and pressurised to approximately 6900 kPa (1000 psi) (full of carbon dioxide). The cell was then heated to 60 C. for 40 hrs and then allowed to cool. When the pressure had dropped below 13800 kPa (2000 psi), the cell was vented into ether (100 ml), the cell was opened once atmospheric pressure was reached and washed out with a further quantity of ether (20 ml). The extracts were combined and washed with water (100 ml). The resultant aqueous layer was further extracted with ether (2×100 ml) and the organic fractions combined, dried ($MgSO_4$) and concentrated in vacuo to give the crude product. The product was purified by flash column chromatography on silica gel, eluting with hexane to give a white crystalline solid (105 mg, 0.60 mmol, 60%); SH (250 MHz; $CDCl_3$) 7.56–7.61 (4H, m, o-Ph), 7.33–7.43 (6H, m, m/pPh); $\delta_C$ 131.7 (o-C), 128.5 (m-Ph), 128.4 (p-Ph), 123.4 (quaternary Ph), 89.5 (alkyne).

The reaction was also conducted at higher temperatures (80 and 100 C.) by the same procedure, except that the cell was filled approximately three quarters full with carbon dioxide and then brought to the reaction temperature. Once at this temperature, the pressure was increased until approx. 25600 kPa (4000 psi).

EXAMPLE 8

3-Methylindole

Di(1H,2H,2H-perfluorooctyl)phenylphosphine (80 mg, 0.1 mmol), palladium (II) acetate (11 mg, 0.05 mmol), N-allyl-2-iodoaniline (259 mg, 1 mmol) and triethylamine (0.15 ml, 1.1 mmol) were placed in a 10 ml stainless steel cell. The cell was sealed and pressurised to approximately 5520 kPa (800 psi) (i.e. full of carbon dioxide). The cell was then heated to 100 C. for 64 hrs and then allowed to cool. When the pressure had dropped below 13800 kPa (2000 psi), the cell was vented into ether (100 ml), the cell was opened once atmospheric pressure was reached and washed out with dichloromethane (20 ml). The organic fractions were combined and concentrated in vacuo to give the crude product. The product was purified by flash column chromatography on silica gel, eluting with 20% ether in hexane to give a white crystalline solid (49 mg, 0.37 mmol, 37%); $\delta_H$ (250 MHz; $CDCl_3$) 7.85 (1H, br, NH), 7.63 (1H, m, H7), 7.34 (1H, m, H4), 7.15–7.26 (2H, m, H5 and H6), 6.97 (1H, s, NHCH), 2.38 (3H, s, Me).

EXAMPLE 9

Biphenyl

Bis{di(1H,1H,2H,2H-perfluorooctyl) phenylphosphino}palladium dichloride (89 mg, 0.05 mmol), iodobenzene (0.11 ml, 1 mmol), phenylboronic acid (122 mg, 1 mmol) and triethylamine (0.15 ml, 1.1 mmol) were placed in a 10 ml stainless steel cell. The cell was sealed and pressurised to approximately 5520 kPa (800 psi) (i.e. full of carbon dioxide). The cell was then heated to 100 C. for 64 hrs and then allowed to cool. When the pressure had dropped below 13800 kPa (2000 psi) the cell was vented into ether (100 ml), the cell was opened once atmospheric pressure was reached and washed out with dichloromethane (20 ml). The organic fractions were combined and concentrated in vacuo to give the crude product. The product was purified by flash column chromatography on silica gel, eluting with hexane to give a white crystalline solid (80 mg, 0.52 mmol, 52%); $\delta_H$ (250 MHz; $CDCl_3$) 7.34–7.65 (10H, m, aryl).

EXAMPLE 10

2-Phenylthiophene

Bis{di(1H,1H,2H,2H-perfluorooctyl) phenylphosphino}palladium dichloride (89 mg, 0.05 mmol), iodobenzene (0.11 ml, 1 mmol), thiophene-2-boronic acid (128 mg, 1 mmol) and triethylamine (0.15 ml, 1.1 mmol) were placed in a 10 ml stainless steel cell. The cell was sealed and pressurised to approximately 5520 kPa (800 psi) (i.e. full of carbon dioxide). The cell was then heated to 100 C. for 64 hrs and then allowed to cool. When the pressure had dropped below 13800 kPa (2000 psi) the cell was vented into ether (100 ml), the cell was opened once atmospheric pressure was reached and washed out with dichloromethane (20 ml). The organic fractions were combined and concentrated in vacuo to give the crude product. The product was purified by flash column chromatography on silica gel, eluting with hexane to give a white crystalline solid (78 mg, 0.49 mmol, 49%); $\delta_H$ (250 MHz; $CDCl_3$) 7.09–7.66 (8H, m, aryl and thienyl).

EXAMPLES 11 to 17

Heck Reactions

The following reactions and conditions were used: iodide (1.0 mmol), alkene (1.0 mmol), triethylamine (1.1 mmol), catalyst (5 mol %), 40 h, 100° C.

A typical procedure was as follows: bis(1H,1H,2H, 2Hperfluorooctyl)phenylphosphine (80 mg, 0.1 mmol), palladium (II) acetate (11 mg, 0.05 mmol), iodobenzene (0.11 ml, 1 mmol), methyl acrylate (0.11 ml, 1 mmol) and triethylamine (0.15 ml, 1.1 mmol) were placed in a 10 ml stainless steel cell. The cell was sealed and pressurised to approximately 6900 kPa (1000 psi) (about ¾ full of liquid carbon dioxide). The suspended reagents were magnetically stirred and afforded a dark red-coloured medium as the cell was heated to 100° C. The reagents were stirred at this temperature for 40 h when a crystalline deposit formed on the sapphire window. The cell was then cooled, and when the pressure had dropped below 13800 kPa (2000 psi), the cell was vented into ether (100 ml), the cell was opened once atmospheric pressure was reached and washed out with a quantity of dichloromethane (10 ml). The organic fractions were combined and concentrated in vacuo to give the crude product. The product was purified by flash column chromatography on silica gel, eluting with dichloromethane to give trans-methylcinnamate as a white crystalline solid (157 mg, 0.97 mmol, 97%); [CAS 1754-62-7] mp 35–37° C.

This and other Heck reactions are tabulated below.

mmol), iodobenzene (0.02 ml, 0.22 mmol), REM Resin (Aldrich, 250 mg, 0.25–1.25 mmol) and triethylamine (0.03 ml, 0.22 mmol) were placed in a 10 ml stainless steel cell. The cell was sealed and pressurised to approximately 6900 kPa (1000 psi) (about ¾ full of liquid carbon dioxide). The suspended reagents were magnetically stirred and afforded a dark red-coloured medium, the resin remained as a powder in the bottom of the cell. The cell was heated to 100° C. and the reaction mixture stirred at this temperature for 40 h. The cell was then cooled, and when the pressure had dropped below 13800 kPa (2000 psi), the cell was vented into ether (100 ml), the cell was opened once atmospheric pressure was reached and washed out with a quantity of dichloromethane (10 ml). The resulting resin was removed from the cell and washed (Soxhlet) with dichloromethane (100 ml) for 24 h. The resin was then dried under vacuum, to a constant weight, (257 mg) and a portion taken for analysis and release of the product by transesterification. The resin (102 mg, <0.05 mmol) was suspended in a solution of sodium methoxide (8 mg, 0.15 mmol) in methanol (2 ml) and THF (8 ml). The mixture was heated at reflux for 24 h, after cooling the resin was removed by filtration and washed

| Example | Aryl iodide | Alkene | Product | Yield (%) |
|---|---|---|---|---|
| 11 | $O_2N$-C$_6$H$_4$-I | $CH_2=CH-CO_2Me$ | $O_2N$-C$_6$H$_4$-CH=CH-CO$_2$Me | 54 |
| 12 | MeO-C$_6$H$_4$-I | $CH_2=CH-CO_2Me$ | MeO-C$_6$H$_4$-CH=CH-CO$_2$Me | 47 |
| 13 | 2-Me-C$_6$H$_4$-I | $CH_2=CH-CO_2Me$ | 2-Me-C$_6$H$_4$-CH=CH-CO$_2$Me | 32 |
| 14 | MeCO-C$_6$H$_4$-I | $CH_2=CH-CO_2Me$ | MeCO-C$_6$H$_4$-CH=CH-CO$_2$Me | 72 |
| 15 | C$_6$H$_5$-I | $CH_2=CH-CO_2Me$ | C$_6$H$_5$-CH=CH-CO$_2$Me | 97 |
| 16 | C$_6$H$_5$-I | $CH_2=CH-Ph$ | C$_6$H$_5$-CH=CH-Ph | 50 |
| 17 | C$_6$H$_5$-I | $CH_2=CH-C_5H_{11}$ | C$_6$H$_5$-CH=CH-C$_5$H$_{11}$ | 44 |

EXAMPLE 18

Trans-3-phenylacrylic acid methyl ester (trans-methylcinnamate)

Bis(1H,1H,2H,2H-perfluorooctyl)phenylphosphine (14.5 mg, 0.019 mmol), palladium (II) acetate (2 mg, 0.009 with methanol (5 ml) and ether (5 ml). The filtrate was concentrated in vacuao and the product purified by flash chromatography on silica gel, eluting with 10% ether in hexane to give the title compound as a white crystalline solid (6 mg, 0.037 mmol, >74%). [CAS 1754-62-7] mp 35–37° C.

EXAMPLE 19

Copolymerisation of 1 and 4

A mixture of monomers 1 and 4 (55:45 wt/wt) was purified by passing though a neutral alumina column. This mixture (2.0 g) and 2,2'-azobisisobutyronitrile (AIBN, 0.16 g) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=22° C., P=64 bar) and stirring was commenced using a PTFE-coated magnetic str bar. Under these initial conditions, much of the monomer mixture was insoluble in the liquid $CO_2$ phase, and the reaction mixture existed as a white, cloudy suspension. The reactor was heated to achieve the required polymerisation conditions (65° C., P=290±10 bar) and a fine white precipitate began to form in the reactor after around 90 min. The reactorwas left stirring at 65° C. for24 h, after which the system was cooled to ambient temperature. The $CO_2$ was vented slowly though acetone to trap any polymer/monomer that might otherwise escape during venting. The polymer was *removed from the reactor as a dry, white, free-flowing powder. The reactor was then rinsed with acetone to collect any residual solids. The polymeric product was washed by suspension in a solvent (~25 mL) followed by centrifuging and decanting. This procedure was repeated twice, both with THF and with methanol. The polymer was then left under acetone overnight, resuspended twice in ethanol, centrifuged, decanted, and dried under vacuum at 50° C. There was no apparent weight loss after the washing procedure, and no soluble polymer fraction was detected. The purified polymer was isolated as a white powder (1.78 g, 89%). Found: C, 90.2; H, 8.3; Calculated: C, 91.6; H, 8.4%. IR (KBr)/cm$^{-1}$: 3450, 3018, 2964, 2925, 1603, 1511, 1486, 1449, 903, 834, 795, 710.

EXAMPLE 20

Copolymerisation of 1 and 4

A mixture of monomers 1 and 4 (55:45 wt/wt) was purified by passing though a neutral alumina column. This mixture (4.34 g) and AIBN (0.35 g) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=24° C., P=95 bar) and stirring was commenced using a PTFE-coated magnetic stir bar. Under these initial conditions, much of the monomer mixture was insoluble in the liquid $CO_2$ phase, and the reaction mixture existed as a white, cloudy suspension. The reactor was heated to achieve the required polymerisation conditions (65° C., P=318±10 bar) and a fine white precipitate began to form in the reactor after around 30 min. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The same purification procedures were used as for Example 19. The purified polymer was isolated as a white powder (4.29 g, 99%). Found: C, 88.7; H, 8.0; Calculated: C, 91.6; H, 8.4%. IR (KBr)/cm$^{-1}$: 3450, 3018, 2964, 2925, 1603, 1511, 1486, 1449, 903, 834, 795, 710.

EXAMPLE 21

Copolymerisation of 1 and 4

A mixture of monomers 1 and 4 (80:20 wt/wt) was purified by passing though a neutral alumina column. This mixture (2.0 g) and AIBN (0.16 g) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=24° C., P=66 bar) and stirring was commenced using a PTFE-coated magnetic stir bar. Under these initial conditions, much of the monomer/polymer mixture was insoluble in the liquid $CO_2$ phase, and the reaction mixture existed as a white, cloudy suspension, possibly due to early oligomerisation/polymerisation before the vessel was brought up to the reaction temperature. The reactor was heated to achieve the required polymerisation conditions (65° C., P=333±10 bar) and a fine white precipitate began to form in the reactor after a few minutes. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The same purification procedures were used as for Example 19. The purified polymer was isolated as a white powder (1.84 g, 92%). Found: C, 90.1; H, 8.0; Calculated: C, 91.9; H, 8.0%. IR (KBr)/cm$^{-1}$: 3450, 3018, 2964, 2925, 1603, 1511, 1486, 1449, 903, 834, 795, 710.

EXAMPLE 22

Polymerisation of 2

A mixture of 2 (2.0 g) and AIBN (0.16 g) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=23° C., P=84 bar) and stirring was commenced using a PTFE-coated magnetic stir bar. Under these initial conditions, the monomer was soluble in the liquid $CO_2$ phase, and the reaction mixture was homogeneous. The reactor was heated to achieve the required polymerisation conditions (65° C., P=295±10 bar), whereupon a yellow colour was observed briefly and a fine white precipitate began to form in the reactor after a few minutes. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The same purification procedures were used as for Example 19. The purified polymer was isolated as a white powder (1.60 g, 80%). IR (KBr)/cm$^{-1}$: 2997, 2964, 1737, 1468, 1395, 1356, 1245, 1214, 1150.

EXAMPLE 23

Polymerisation of 3

A mixture of 3 (2.0 g) and AIBN (0.16 g) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=27° C., P=82 bar) and stirring was commenced using a PTFE-coated magnetic stir bar. Under these initial conditions, the monomer was soluble in the liquid $CO_2$ phase, and the reaction mixture was homogeneous. The reactor was heated to achieve the required polymerisation conditions (65° C., P=300±10 bar), whereupon a yellow colour was observed briefly and a fine white precipitate began to form in the reactor after around 30 minutes. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The same purification procedures were used as for Example 19. The purified polymer was isolated as a white powder (1.87 g, 93.5%). Found: C, 62.3; H, 7.6; Calculated: C, 63.9; H, 7.8%. IR (KBr)/cm$^{-1}$: 2970, 1735, 1650, 1559, 1542, 1517, 1490, 1461, 1264, 1152.

EXAMPLE 24

Copolymerisation of 1, 4 and 5

A mixture of monomers 1 (1.02 g), 4 (0.83 g) and 5 (0.28 g) and AIBN (0.16 g) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=25° C., P=106 bar) and stirring was commenced using a PTFE-coated magnetic stir bar. Under these initial conditions, much of the monomer mixture was insoluble in the liquid $CO_2$ phase, and the reaction mixture existed as a white, cloudy suspension. The reactor was heated to achieve the required polymerisation conditions (65° C., P=327±10 bar) and a fine white precipitate began to form in the reactor after around 30 min. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The same purification procedures were used as for Example 19. The purified polymer was isolated as a white powder (1.95 g, 92%). Found: C, 87.64; H, 8.02; Cl, 2.70; Calculated: C, 89.55; H, 8.13%; Cl, 2.32. IR (KBr)/cm$^{-1}$: 3450, 3018, 2964, 2925, 1603, 1511, 1486, 1449, 903, 834, 795, 710.

EXAMPLE 25

Copolymerisation of 1, 4 and 6

A mixture of monomers 1 (0.99 g), 4 (0.81 g) and 6 (0.20 g) and AIBN (0.16 g) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=26° C., P=81 bar) and stirring was commenced using a PTFE-coated magnetic stir bar. Under these initial conditions, much of the monomer mixture was insoluble in the liquid $CO_2$ phase, and the reaction mixture existed as a white, cloudy suspension. The reactor was heated to achieve the required polymerisation conditions (65° C., P=286±10 bar) and a fine white precipitate began to form in the reactor after a few minutes. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The same purification procedures were used as for Example 19. The purified polymer was isolated as a white powder (1.79 g, 90%). Found: C, 86.3; H, 7.6; Calculated: C, 87.4; H, 7.6%. IR (KBr)/cm$^{-1}$: 3450, 3018, 2964, 2925, 1603, 1511, 1486, 1449, 903, 834, 795, 710.

EXAMPLE 26

Copolymerisation of 1, 4 and 7

A mixture of monomers 1 (0.99 g), 4 (0.81 g) and 7 (0.20 g) and AISN (0.16 g) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=22° C., P=85 bar) and stirring was commenced using a PTFE-coated magnetic stir bar. Under these initial conditions, much of the monomer mixture was insoluble in the liquid $CO_2$ phase, and the reaction mixture existed as a white, cloudy suspension. As the reactor was heated, the solution gradually became homogeneous (T>37° C., P>179 bar). A deep red colour was formed under the polymerisation conditions (65° C., P=332±10 bar), followed by the formation of a fine in the reactor after a few minutes. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The same purification procedures were used as for Example 19. The purified polymer was isolated as a white powder (1.79 g, 90%). Found: C, 89.5; H, 8.7; Calculated: C, 90.2; H, 8.8%. IR (KBr)/cm$^{-1}$: 2854, 1731, 1603, 1486, 1449, 901, 795, 708.

EXAMPLE 27

Copolymerisation of 1, 4 and 8

A mixture of monomers 1 (0.99 g), 4 (0.81 g) and 8 (0.20 g) and AIBN (0.16 g) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=28° C., P=103 bar) and stirring was commenced using a PTFE-coated magnetic stir bar. Under these initial conditions, much of the monomer mixture was insoluble in the liquid $CO_2$ phase, and the reaction mixture existed as a white, cloudy suspension. The reactor was heated to achieve the required polymerisation conditions (65° C., P=276±10 bar) and a fine white precipitate began to form in the reactor after a few minutes. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The same purificaton procedures were used as for Example 19. The purified polymer was isolated as a white powder (1.80 g, 90%). Found: C, 85.1; H, 7.8; N, 0.9; S, 0.4; Calculated: C, 85.5; H, 7.7; N, 0.2; S, 0.5. IR (KBr)/cm$^{-1}$: 3020, 2966, 2927, 1733, 1601, 1484, 1447, 1240, 1213, 1154.

EXAMPLE 28

Copolymerisation of 1, 4 and 9

A mixture of monomers 1 (1.28 g), 4 (0.32 g) and 9 (0.40 g) and AIBN (0.16 g) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=29° C., P=86 bar) and stirring was commenced using a PTFE-coated magnetic stir bar. Under these initial conditions, the monomer mixture was soluble in the liquid $CO_2$ phase, and the reaction mixture existed as a homogeneous solution. The reactor was heated to achieve the required polymerisation conditions (65° C., P=282±10 bar) and a pale yellow colour was observed, followed by the formation of a fine white precipitate in the reactor after a few minutes. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The same purification procedures were used as for Example 19. The purified polymer was isolated as a white powder (1.82 g, 91%). Found: C, 80.4; H, 7.6; Calculated: C, 84.8; H, 7.8%. IR(KBr)/cm$^{-1}$: 3047, 3016, 2967, 2931, 1700, 1602, 1449, 1214, 907, 799, 712.

EXAMPLE 29

Copolymerisation of 1 and 4 in the presence of surfactant 10

A mixture of monomers 1 and 4 (55:45 wt/wt) was purified by passing though a neutral alumina column. This mixture (2.0 g), AIBN (0.16 g) and surfactant 10 (60 mg) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=22° C., P=75 bar) and stirring was commenced using a PTFE-coated magnetic stir bar. Under these initial conditions, the monomer mixture was emulsified in the liquid $CO_2$ phase, and the reaction mixture existed as a uniform, white opaque emulsion. The reactor was heated to achieve the required polymerisation conditions (65° C., P=310±10 bar) and polymerisation was carried out. The emulsion persisted during polymerisation and a uniform white appearance was observed throughout. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The reactor was then rinsed with acetone to collect any residual solids. The same purification procedures were used as for Example 19. There was no apparent weight loss after the washing procedure, and no soluble polymer fraction was detected. The purified polymer was isolated as a white powder (1.92 g, 96%). Found: C, 89.9; H, 8.3; Calculated: C, 91.6; H, 8.4%. IR (KBr)/cm$^{-1}$: 3450, 3018, 2964, 2925, 1603, 1511, 1486, 1449, 903, 834, 795, 710.

EXAMPLE 30

Copolymerisation of 1 and 4 in the Presence of Surfactant 10

A mixture of monomers 1 and 4 (80:20 wt/wt) was purified by passing though a neutral alumina column. This mixture (2.0 g), AIBN (0.16 g) and surfactant 10 (60 mg) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=27° C., P=77 bar) and stirring was commenced using a PTFE-coated magnetic stir bar. Under these initial conditions, the monomer mixture was emulsified in the liquid $CO_2$ phase, and the reaction mixture existed as a uniform, white opaque emulsion. The reactor was heated to achieve the required polymerisation conditions (65° C., P=286±10 bar) and polymerisation was carried out. The emulsion persisted during polymerisation and a uniform white appearance was observed throughout. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The reactor was then rinsed with acetone to collect any residual solids. The same purification procedures were used as for Example 19. There was no apparent weight loss after the washing procedure, and no soluble polymer fraction was detected. The purified polymer was isolated as a white powder (1.90 g, 95%). Found: C, 88.3; H, 7.9; Calculated: C, 91.9; H, 8.0%. IR (KBr)/cm$^{-1}$: 3450, 3018, 2964, 2925, 1603, 1511, 1486, 1449, 903, 834, 795, 710.

EXAMPLE 31

Copolymerisation of 1, 4+9 in the Presence of Surfactant 10

A mixture of monomers 1 (1.28 g), 4 (0.32 g), 9 (0.40 g), AIBN (0.16 g) and surfactant 10 (60 mg) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=25° C., P=102 bar) and stirring was commenced using a PTFE coated magnetic stir bar. Under these initial conditions, the monomer mixture was emulsified in the liquid $CO_2$ phase, and the reaction mixture existed as a uniform, white opaque emulsion. The reactor was heated to achieve the required polymerisation conditions (65° C., P=328±10 bar) and polymerisation was carried out. The emulsion persisted during polymerisation and a uniform white appearance was observed throughout. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, white, free-flowing powder. The same purification procedures were used as for Example 19. The purified polymer was isolated as a white powder (1.94 g, 97%). Found: C, 80.4; H, 7.6; Calculated: C, 84.8; H, 7.8%. IR (KBr)/cm$^{-1}$: 3047, 3016, 2967, 2931, 1700, 1602, 1449, 1214, 907, 799, 712.

EXAMPLE 32

Copolymerisation of 1, 4+9 in the Presence of Surfactant 10 and Disperse Red 1 (11)

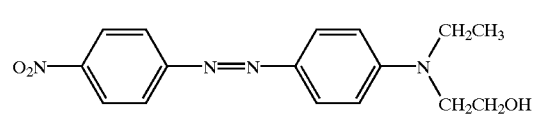

A mixture of monomers 1 (1.28 g), 4 (0.32 g) and 9 (0.40 g), AIBN (0.16 g), Disperse Red 1 (20 mg), and surfactant 10 (60 mg) was added to a 10 mL high pressure reactor, equipped with a sapphire window for the observation of phase behaviour. The reactor was purged with a slow flow of $CO_2$ for 20 min, after which time the vessel was filled with liquid $CO_2$ (T=28° C., P=85 bar) and stirring was commenced using a PTFE-coated magnetic stir bar. Under these initial conditions, the monomer mixture was emulsified in the liquid $CO_2$ phase, and the reaction mixture existed as a uniform, pale red, opaque emulsion. Nearly all of the dye, Disperse Red 1, which is insoluble in $CO_2$ under these conditions, was dissolved in the emulsified monomer phase. The reactor was heated to achieve the required polymerisation conditions (65° C., P=326±10 bar) and polymerisation was carried out. The emulsion persisted during polymerisation and a uniform opaque red appearance was observed throughout. The reactor was left stirring at 65° C. for 24 h, after which the system was cooled to ambient temperature. The $CO_2$ was vented slowly though acetone to trap any polymer/monomer that might otherwise escape during venting. The polymer was removed from the reactor as a dry, pale red, free-flowing powder. (1.90 g, 92%). Found: C, 80.4; H, 7.6; N, 1.5; Calculated: C, 84.1; H, 7.8; N, 0.5%. IR (KBr)/cm$^{-1}$: 3047, 3016, 2967, 2931, 1700, 1602, 1449, 1214, 907, 799, 712. The pale red polymer was treated by Soxhlet extraction (95° C., toluene, 72 h). After extraction, an off-white polymer was obtained, demonstrating that a large percentage of the dye was extractable from the cross-linked matrix.

Scanning Electron Microscopy showed that the polymer products obtained in each of Examples 19 to 32 were substantially uniform, substantially spherical particles.

We claim:

1. A process for the transformation of an organic molecule catalyzed by a ligand-metal complex, wherein the metal is pd which is conducted in compressed $CO_2$ as a solvent and wherein the complex comprises a perfluorinated group.

2. The process according to claim 1, wherein the ligand has the formula X—YR$_1$R$_2$R$_3$, in which X is O, S or Se, or represents an unshared pair of electrons, Y is P or As, and R$_1$, R$_2$ and R$_3$ are each an organic group of which at least one is at least partially perfluorinated.

3. The process according to claim 2, wherein R$_1$, R$_2$ and R$_3$ are each C$_{4-8}$ alkyl.

4. The process according to claim 2, wherein X is an unshared pair of electrons.

5. The process according to claim 2, wherein Y is P.

6. The process according to claim 1, wherein the transformation is selected from the group consisting of hydrogenation, hydroboration, hydrosilylation, hydrocyanation, hydroformylation, allylic substitution, carbonylation, cross-coupling processes, cyclisation processes, conjugate addition, oxidation and epoxidation.

7. The process according to claim 6, wherein the transformation comprises a Heck, Susuki, Sanogashira or Stille coupling.

8. The process according to claim 1, wherein the transformation is conducted on a solid phase.

9. The process according to claim 1, wherein the organic molecule undergoing transformation is immobilized.

10. A process which is a Heck, Suzuki, Sonogashira or Stille coupling reaction catalysed by a ligand-Pd complex, which is conducted in compressed $CO_2$ as a solvent and wherein the complex comprises a perfluorinated group.

11. The process according to claim 10, wherein the ligand has the formula X=YR$_1$R$_2$R$_3$, in which X is O, S or Se, or represents an unshared pair of electrons, Y is P or As, and R$_1$, R$_2$ and R$_3$ are each an organic group of which at least one is at least partially perfluorinated.

12. The process according to claim 11, wherein R$_1$, R$_2$ and R$_3$ are each C$_{4-8}$ alkyl.

13. The process according to claim 11, wherein X is an unshared pair of electrons.

14. The process according to claim 11, wherein Y is P.

15. The process according to claim 11, wherein any of R$_1$, R$_2$ and R$_3$ comprise a Pd-chelating group.

16. The process according to claim 15, wherein the Pd-chelating group comprises P, N, O, S, or AS.

17. The process according to claim 10, wherein a component of the coupling reaction is immobilized.

18. The process according to claim 10, wherein the coupling results in allylic substitution, cross-coupling, cyclisation, or conjugate addition.

19. The process according to claim 10, which is a Heck reaction.

* * * * *